US009801685B2

(12) United States Patent
Nguyen et al.

(10) Patent No.: US 9,801,685 B2
(45) Date of Patent: Oct. 31, 2017

(54) CONNECTION METHOD FOR MEMS NAVIGATION UNIT FOR COMPUTER-ASSISTED SURGERY

(71) Applicant: ORTHOSOFT INC., Montreal (CA)

(72) Inventors: Tin Nguyen, Laval (CA); Yvan Léone, Montréal (CA); Benoit Pelletier, Laval (CA)

(73) Assignee: ORTHOSOFT INC., Montréal (CA)

(*) Notice: Subject to any disclaimer, the term of this patent is extended or adjusted under 35 U.S.C. 154(b) by 19 days.

(21) Appl. No.: 13/724,060

(22) Filed: Dec. 21, 2012

(65) Prior Publication Data

US 2013/0165947 A1 Jun. 27, 2013

Related U.S. Application Data

(60) Provisional application No. 61/579,783, filed on Dec. 23, 2011.

(51) Int. Cl.

*A61B 19/00* (2006.01)
*A61B 17/00* (2006.01)
(Continued)

(52) U.S. Cl.

CPC ............ *A61B 19/201* (2013.01); *A61B 34/20* (2016.02); *A61B 2017/00477* (2013.01); *A61B 2034/2048* (2016.02); *A61B 2090/3983* (2016.02)

(58) Field of Classification Search

CPC ........ A61B 2019/5483; A61B 19/5244; A61B 2019/5255; A61B 2019/5251;
(Continued)

(56) References Cited

U.S. PATENT DOCUMENTS

2004/0171930 A1 9/2004 Grimm et al.
2007/0287910 A1 12/2007 Stallings et al.
(Continued)

FOREIGN PATENT DOCUMENTS

DE 29600990 4/1996
FR 2859377 3/2005
WO WO2004017842 3/2004

OTHER PUBLICATIONS

Layton Carter Hale, Principles and Techniques for Designing Precision Machines, Ph. D. Thesis, Feb. 1999.*
(Continued)

*Primary Examiner* — Gary Jackson
*Assistant Examiner* — Scott T Luan
(74) *Attorney, Agent, or Firm* — Norton Rose Fulbright Canada LLP

(57) ABSTRACT

A computer-assisted surgery (CAS) navigation assembly comprises a micro-electromechanical sensor (MEMS) navigation unit having one or more MEMS to provide at least orientation data. A support receives the MEMS navigation unit therein, the support being adapted to be mounted on the instrument in a fixed orientation relative to established navigated features of the instrument. At least two mating ball-in-socket features are disposed between the MEMS navigation unit and the support at opposed ends thereof for releasably engaging the MEMS navigation unit in precise orientational alignment within the receptacle, the at least two mating ball-in-socket features comprising catches aligned along an axis extending between the opposed ends, at least one of the catches being a biased catch. A method of connecting a MEMS navigation unit with a mating support fixed to a CAS instrument navigated by the CAS system is also provided.

17 Claims, 5 Drawing Sheets

30
SEE FIG. 6c
14
12
32
34
SEE FIG. 6d
XY

(51) Int. Cl.
*A61B 90/00* (2016.01)
*A61B 34/20* (2016.01)

(58) Field of Classification Search
CPC .... A61B 2019/5272; A61B 2019/5445; A61B 2017/00477; A61B 19/201; A61B 34/20; A61B 2090/3983; A61B 2034/2048
See application file for complete search history.

(56) References Cited

U.S. PATENT DOCUMENTS

| | | | | |
|---|---|---|---|---|
| 2010/0100081 | A1* | 4/2010 | Tuma et al. | 606/1 |
| 2011/0218458 | A1 | 9/2011 | Valin et al. | |
| 2011/0257653 | A1 | 10/2011 | Hughes et al. | |
| 2011/0275957 | A1 | 11/2011 | Bhandari | |
| 2012/0232834 | A1 | 9/2012 | Roche et al. | |
| 2013/0079790 | A1* | 3/2013 | Stein | A61F 2/4611 606/102 |

OTHER PUBLICATIONS

European Search Report, Application No. 12859012.2, Dec. 23, 2015.

* cited by examiner

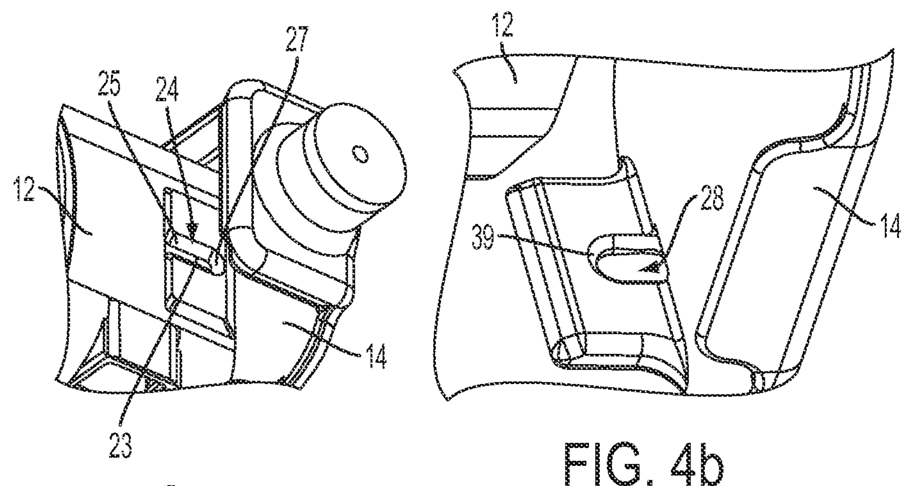
FIG. 4a
FIG. 4b
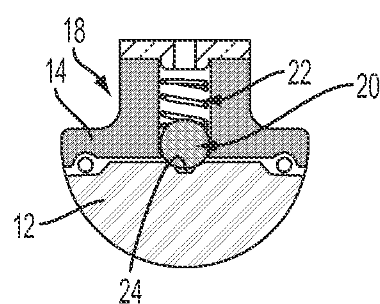
FIG. 5

CONNECTION METHOD FOR MEMS NAVIGATION UNIT FOR COMPUTER-ASSISTED SURGERY

CROSS-REFERENCE TO RELATED APPLICATION

The present patent application claims priority on U.S. Provisional Application No. 61/579,783, incorporated herewith by reference.

TECHNICAL FIELD

The present application relates generally to computer-assisted orthopedic surgery systems using micro-electromechanical sensors.

BACKGROUND

The use of micro-electromechanical sensors (MEMS), rather than more traditional optically-tracked sensors for example, for the purposes of communicating with a computer-assisted surgery (CAS) system such as to navigate tools, bones, reference markers, etc. within the surgical field is becoming more desirable because such MEMS sensors are not limited by line-of-sight requirements of previously used optical sensors. These MEMS, which may for example include accelerometers and/or gyroscopes, are able to wirelessly communicate with the CAS system with which they are employed, or are equipped with a processor and user interface providing guidance to a user, i.e., the MEMS unit is part of a portable CAS system that is directly on the CAS instrument. Accordingly, the CAS system is able to determine at least orientation information of the MEMS unit, and therefore able to locate and track (i.e. navigate) the tool or bone to which the MEMS unit is fastened.

One of the steps required to navigate any tracked bone reference or surgical tool using a CAS system, including one which employs MEMS, is to "calibrate" the CAS instrument (ex: either a bone reference or tool) by precisely locating the position and/or orientation of the sensor relative that of the CAS instrument to which it is fastened. In the event that the sensor is detached from the CAS instrument, it is typically necessary to re-calibrate the assembly once the sensor is again fixed in its normal position relative to the instrument.

It may be desirable to be able to switch MEMS from one CAS instrument to another, however this becomes problematic because each time the MEMS is removed and then re-fastened, either onto another instrument or even back onto the same original instrument from which it was detached, a new calibration step must be performed in order to ensure that the exact relative position of the MEMS and the CAS instrument to which it is fastened are determined by the CAS system.

Accordingly, there is a need for a MEMS-navigated CAS instrument which enables the MEMS to be readily removed and re-attached to the instrument with repeatable precision and accuracy such that the relative alignment and orientation of the instrument and the MEMS will remain constant, thereby avoiding the need to re-calibrate the entire instrument in the event that the MEMS sensor is removed and/or re-attached.

SUMMARY

It is therefore an object of the present invention to provide an improved MEMS-navigated CAS instrument and an associated method of connecting such a MEMS navigation unit to such a CAS instrument.

Therefore, in accordance with one aspect of the present disclosure, there is provided a computer-assisted surgery (CAS) navigation assembly adapted for navigating an instrument, the navigation assembly comprising: a micro-electromechanical sensor (MEMS) navigation unit having one or more MEMS to provide at least orientation data; a support receiving the MEMS navigation unit therein, the support being adapted to be mounted on the instrument in a fixed orientation relative to established navigated features of the instrument; and at least two mating ball-in-socket features disposed between the MEMS navigation unit and the support at opposed ends thereof for releasably engaging the MEMS navigation unit in precise orientational alignment within the receptacle, the at least two mating ball-in-socket features comprising catches aligned along an axis extending between the opposed ends, at least one of the catches being a biased catch.

Further in accordance with the first aspect, the support comprises a receptacle for receiving a portion of the MEMS navigation unit therein, the ball-in-socket features being located in the receptacle.

Still further in accordance with the first aspect, the receptacle comprises at least one planar surface, with the MEMS navigation unit being in coplanar abutment with the at least one planar surface when releasably engaged in the fixed orientation.

Still further in accordance with the first aspect, the receptacle comprises at least two planar surfaces for coplanar with corresponding surfaces of the MEMS navigation unit, the two planar surfaces being transverse with respect to one another.

Still further in accordance with the first aspect, the receptacle comprises three planar surfaces arranged in a U, with normals of the planar abutment surfaces being transverse relative to said axis.

Still further in accordance with the first aspect, one of the catches is a fixed catch.

Still further in accordance with the first aspect, the fixed catch has a geometry defined by a sphere quarter merging with a half-cylinder.

Still further in accordance with the first aspect, the fixed catch protrudes from the MEMS navigation unit.

Still further in accordance with the first aspect, the biased catch is part of the support, and wherein a socket cooperating with the biased catch is on the MEMS navigation unit.

Still further in accordance with the first aspect, the socket is defined a raised plateau on the MEMS navigation unit.

Still further in accordance with the first aspect, the MEMS navigation unit comprises a ramp portion adjacent to the socket and transitioning to the raised plateau for guiding the biased catch into the socket during assembly.

Still further in accordance with the first aspect, an elastomer surrounds a periphery of the raised plateau in the releasable engagement.

Still further in accordance with the first aspect, a latch feature is on the support for latching engagement of the MEMS navigation unit to the support.

Still further in accordance with the first aspect, the latch feature comprises a lever for disengagement of the latch feature from the MEMS navigation unit.

In accordance with a second aspect of the present disclosure, there is provided a method of connecting a micro-electromechanical sensor (MEMS) navigation unit of a computer-assisted surgery (CAS) system with a mating support fixed to a CAS instrument navigated by the CAS system, the method comprising: releasably engaging the MEMS navigation unit within the support in precise relative orientational alignment, comprising: aligning and matingly engaging a pair of ball-in-socket features disposed between the MEMS navigation unit and the support at opposed ends thereof, the pair of ball-in-socket features being aligned relative to each; and snap-fitting a biased catch of at least one of said ball-in-socket features within a corresponding socket to constrain and align the relative orientation of the MEMS navigation unit and the support together about a first axis.

Further in accordance with the second aspect, releasably engaging the MEMS navigation unit further comprises abutting at least one planar surface on the MEMS navigation unit against a planar surface on a receptacle of the support, the planar surfaces lying in a substantially common plane to constrain the MEMS navigation unit and the support about at least a second axis.

Still further in accordance with the second aspect, the MEMS navigation unit is latched to the support when releasably engaging the MEMS navigation unit to the support.

BRIEF DESCRIPTION OF THE DRAWINGS

FIG. 4*a* is a second perspective view of the MEMS navigation unit and receptacle of FIG. 3*a*, showing a socket feature for connection of the upper end of the MEMS navigation unit to the receptacle;

FIG. 4*b* is a second perspective view of the receptacle of FIG. 3*b*, showing a socket feature for connection with the lower end of the MEMS navigation unit;

FIG. 5 is a cross-sectional view of the socket connection between the MEMS navigation unit and the mating receptacle;

DETAILED DESCRIPTION

Figure 1:
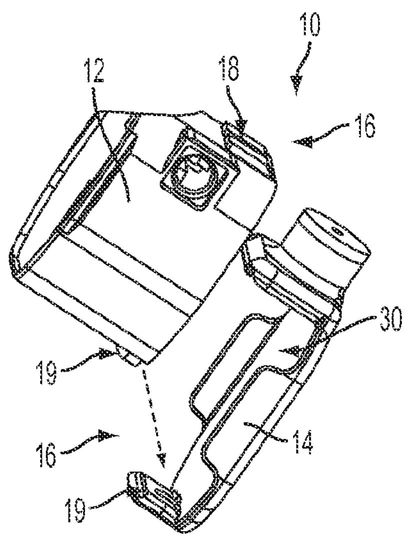
FIG. 1 is a perspective view of a MEMS navigation unit and its mating receptacle, in accordance with one aspect of the present disclosure.

Referring to FIG. 1, computer-assisted surgery (CAS) navigation assembly of the present disclosure includes generally an electronic micro-electromechanical sensor (MEMS) navigation unit 12 and a corresponding connecting support 14 which is adapted to be fixed in place on a CAS instrument, such as a tool or bone reference for example, which is to be navigated using the CAS system. In an embodiment, the connecting receptacle 14 is part of the CAS instrument, whereby reference to the receptacle 14 may include the CAS instrument. The MEMS navigation unit 12 and the receptacle 14 are engaged together in the manner described hereinbelow in further detail. The MEMS navigation unit 12 includes one or more of an accelerometer and/or a gyroscope, and is operable to communicate (e.g., wirelessly or not) with the CAS system with which the navigation assembly 10 is employed. According to another embodiment, the MEMS navigation unit 12 has a processor and visual interface capable of producing navigation output, i.e., without necessarily communicating with a CAS system in that the MEMS navigation unit 12 is the CAS system. Accordingly, the CAS system is able to determine at least orientation information of the MEMS unit, and therefore able to locate and track (i.e. navigate) the CAS instrument to which the MEMS unit 12 is fastened via its connecting dock or receptacle 14. In yet another embodiment, the MEMS navigation unit 12 is of the type having a preset calibration setting, in that its orientation about at least one axis may be known when activated and/or reset.

The support 14 is shown as being a connecting dock or receptacle 14, and is accordingly adapted to be fixed in position and orientation to the CAS instrument to be navigated using the CAS system. For clarity, reference will be made to the support 14 as the receptacle 14, in accordance with the illustrated embodiment. Accordingly, the receptacle 14 is disposed in a fixed orientation relative to the established navigated feature of the instrument to which it is fastened. As described below, the MEMS navigation unit 12 is readily engaged within this receptacle 14 in a manner which provides a quick-connect and quick-disconnect type interconnection, however even given this ease of connection between the two components they are removably engaged together in a fashion which enables their relative alignment and orientation to remain constant and exact each and every time. As such, the MEMS navigation unit 12 can be disconnected from the receptacle 14 and then re-attached thereto, without needing to re-calibrate the entire CAS instrument. This permits, for example, the same MEMS navigation unit 12 to be used during a surgery for navigating several different CAS instruments, each having the same receptacle 14 mounted thereon. A single MEMS navigation unit 12 could therefore be used, if necessary or desirable, to navigate several different instruments within the surgical field, provided of course they do not need to be tracked simultaneously.

Figure 2A:
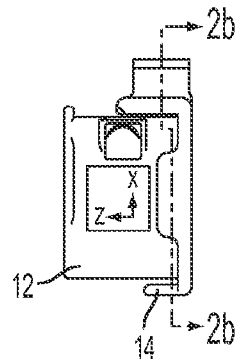
FIG. 2*a* is a side elevation view of the MEMS navigation unit and receptacle of FIG. 1 engaged together.
Figure 2B:
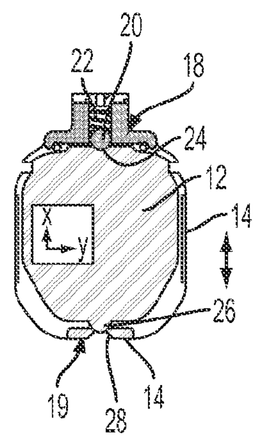
FIG. 2*b* is a cross-sectional view taken through line A-A in FIG. 2*a;*
Figure 3A:
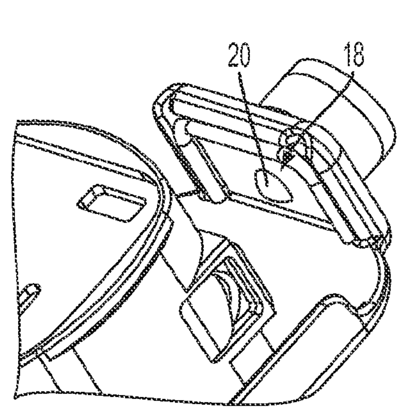
FIG. 3*a* is a first perspective view of the MEMS navigation unit and receptacle of FIG. 1, showing in detail an upper end connection therebetween.
Figure 3B:
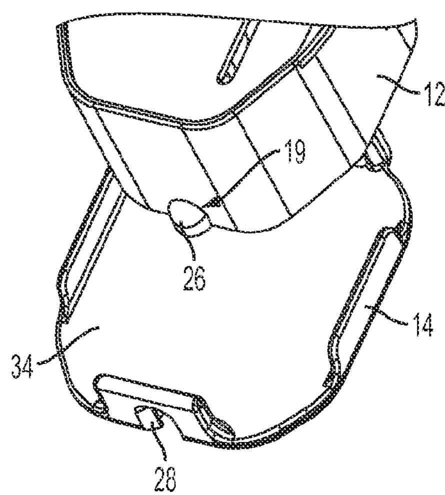
FIG. 3*b* is a first perspective view of the MEMS navigation unit and receptacle of FIG. 1, showing in detail a lower end connection therebetween.

To enable this, the MEMS navigation unit 12 is oriented in an exact position relative to the receptacle 14 using a predetermined and defined system of orthogonal planes, as seen in FIGS. 2*a*-2*b*, which are formed by the shape and configuration of the receptacle 14. This permits a precise and repeatable relation between the MEMS navigation unit 12 and its receptacle 14 to be established each and every time the MEMS navigation unit 12 is engaged in place within the receptacle 14, without requiring a new calibration procedure to be performed.

This precision alignment between the MEMS navigation unit 12 and the receptacle 14 of the CAS instrument is made possible by at least two connection devices 16 and 30, each of which includes cooperating features on each of the receptacle 14 and MEMS navigation unit 12, such as to interconnect the two components of the present navigation assembly 10 in repeatably precise orientation relative to each other about all three orthogonal axes (X, Y and Z).

As seen in FIGS. 2*a*-5, the first connection device 16 includes a pair of ball-in-socket features 18 and 19 which are vertically aligned relative to each other along the X-axis, as seen in FIG. 2*b*. The mating ball-in-socket features 18, 19 between each end of the MEMS navigation unit 12 and the receptacle, forming the first connection device 16, are thus used to constrain and align the relative orientation of the two components about the z-axis.

Referring to the mating ball-in-socket features 18 and 19 in more detail, as seen in FIGS. 3*a*-5, the first ball-in-socket feature 18 comprises a biased catch or catch ball element 20 and the second ball-in-socket feature 19 comprises a fixed catch or ball element 26, each of which engage respective sockets 24, 28 as will be seen.

In the depicted embodiment, best seen in FIG. 2*b* for example, the biased ball-in-socket feature 18 having the biased catch element 20 is located at a top end of the MEMS unit 12 and the receptacle 14; however it may alternately be disposed at the opposite, bottom, end of the components.

As best seen in FIG. 5, the first, or biased, the biased catch element 20 of the ball-in-socket feature 18 may include, in at least this embodiment, a displaceable ball 20 which is biased by a spring 22 or other suitable biasing element (such as an elastomer, etc.). The spring 22 accordingly permits the sprung ball 20 to be forced inwardly away from its normally outwardly biased position (as shown in FIG. 5), in order to be able to interconnect the two components 12 and 14, but returns the ball 20 back into its outwardly biased engaged position. The spring or biasing element 22 is compliant within an established force range such as to permit compression thereof, and thus connection between the ball 20 and its mating socket 24, without the use of high force while nevertheless maintaining the biased contact between the MEMS unit 12 and the receptacle 14.

When the two components 12 and 14 are being interconnected, therefore, once the ball 20 disposed on the receptacle 14 is aligned with its mating socket 24 formed in the MEMS unit 12, the ball 20 accordingly springs back outwardly such as to matingly engage with the socket 24 and thereby interconnect the two components 12 and 14 at this connection point 16. Although in the present embodiment the sprung ball 20 of the biased ball-in-socket feature 18 is disposed on the receptacle and the correspondingly shaped mating socket 24 is disposed in the MEMS unit 12, it is to be understood that the opposite configuration may also be used.

As best seen in FIG. 4*a*, the socket 24 which receives the sprung ball 20 of the biased ball-in-socket feature 18 may comprise be formed in a plateau raised from a remainder of the connection device 16. An open-topped slot 23 is defined in the raised plateau and has an open end 25 and a closed end 27, however circular or other shaped receptacles 24 may also be used. A ramp 27*a* may be formed between the raised plateau and the remainder of the connection device 16. The ramp 27*a* is adjacent to closed end 27. The biased ball, or catch element, 20 of the mating ball-in-socket feature 18 accordingly enables a "snap"-fit connection between the MEMS navigation unit 12 and the receptacle 14 at the respective end at which this feature 18 is disposed. It is pointed out that, despite a full sphere being illustrated being shown in the illustrated embodiment, other geometries may be used, such as a frusto-sphere, etc. The expression "ball" covers segments of a ball, of a sphere including at least a portion of the outer surface of the ball, sphere, etc. The expression "socket" covers a concavity shaped to have some mating contact with the ball.

As noted above, and seen in FIGS. 3*b* and 4*b*, the opposed ball-in-socket feature 19 of the first connection device 16, which is disposed at the opposite end of the two components 12 and 14 from the biased ball-in-socket feature 18, includes a protruding fixed (i.e. rigid or non-biased) catch element 26 that is integrally formed with the base of the MEMS unit 12. The rigid catch element 26 is received within its corresponding mating socket 28 formed in the receptacle 14. However, the opposite configuration may also be used (i.e. the protruding fixed catch element 26 may be located on the receptacle 14 and the mating socket 28 may be formed in the body of the MEMS unit 12). As observed in FIG. 3*b*, the rigid catch element 26 has a ball portion and more specifically a quarter of a sphere or ball, with a half-cylinder base, although a ball, a frusto-sphere or half-ball, etc could be used, all of which fall within the scope and definition of ball-and-socket feature. The combination of the ball and half-cylinder base may provide additional contact surface between components of the ball-in-socket feature 19.

Figure 7A:
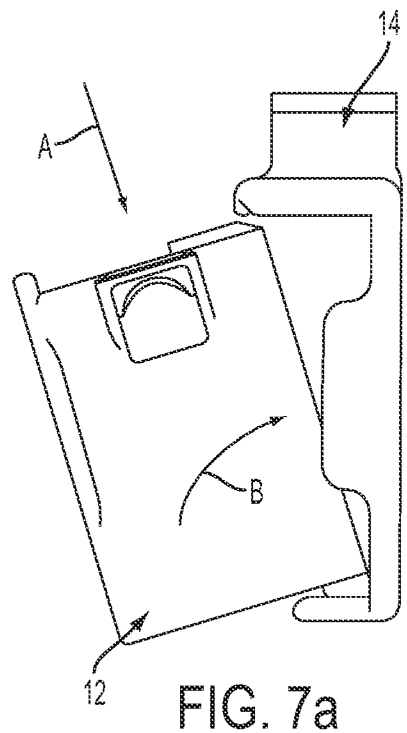
FIG. 7*a* is a side elevational view of the MEMS navigation unit being connected with the mating receptacle.
Figure 7B:
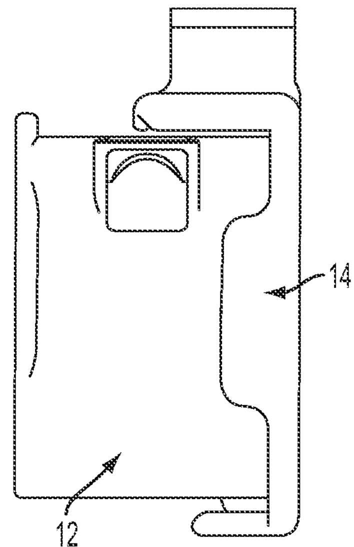
FIG. 7*b* is a side elevational view of the MEMS navigation unit being located in position within the mating receptacle.

Regardless, as shown in FIGS. 7*a*-7*b*, the rigid ball-in-socket connection feature 19 is the first of the two alignment features 18, 19 to be engaged when connected the MEMS unit 12 into the receptacle 14 (step "A"), following which the biased ball-in-socket feature 18 is engaged by pivoting the MEMS navigation unit 12 inward into the receptacle 14 (step "B") until the point where the biased alignment feature 18 snaps into engagement, thereby securing the two components 12, 14 together in mated engagement as shown in FIG. 7*b*.

In another possible embodiment, however, the first connection device 16 may comprise two biased ball-in-socket features 18, rather than having one fixed feature 19 and one biased feature 18 as per the depicted embodiment described above. Regardless, the first connection device 16 includes a pair of mating ball-in-socket features which releasably interconnect the MEMS navigation unit 12 and the receptacle 14 and which are vertically aligned relative to each other along the X-axis, such as to constrain and align the relative orientation of the two components 12, 14 about the z-axis (see FIG. 2*a*).

As noted above, the MEMS navigation unit 12 and the receptacle 14 are interconnected in a repeatably precise orientation relative to each other by at least two connection devices 16 and 30, each of which includes shared and cooperating features on each of the receptacle 14 and MEMS navigation unit 12.

Figure 6A:
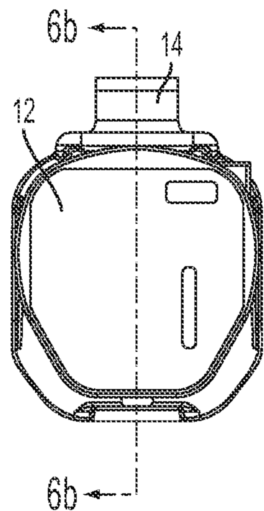
FIG. 6*a* is front elevation view of the mated MEMS navigation unit and the receptacle.
Figure 6B:
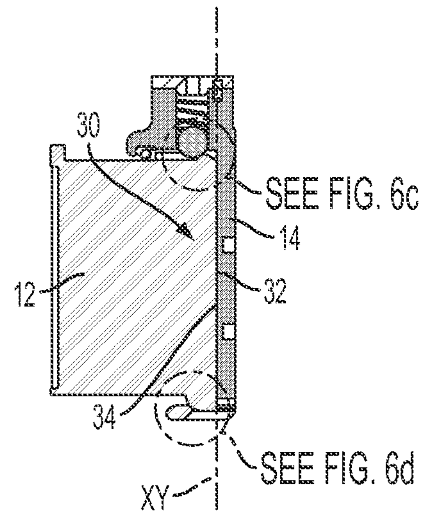
FIG. 6*b* is a cross-sectional view taken through line B-B in FIG. 6*a;*

Referring now to FIGS. 6*a*-6*d*, the second of these connection devices 30 constrains the relative orientation of the MEMS navigation unit 12 and the receptacle 14 about the X-axis and the Y-axis. This second connection device 30 comprises the abutting contact between the rear planar surface 32 of the MEMS navigation unit 12 and the front planar surface 34 within the receptacle 14. These two planar surfaces 32, 34 accordingly abut and lay flat one on top of the other, albeit in a vertical orientation, when the MEMS navigation unit 12 and the receptacle 14 are engaged together as shown in FIG. 6*b*. By abutting the two planar surfaces 32 and 34 such that they lie in a substantially common plane XY as shown in FIG. 6*b*, in as much as two solid planar surfaces can, the relative orientation of the MEMS unit 12 and the receptacle 14 is thereby constrained about the X and Y axes. The U-shape of the receptacle 14 is well suited for retaining the MEMS unit 12.

Figure 6C:
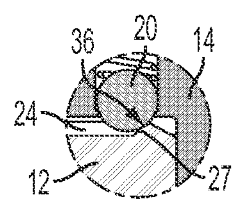
FIG. 6*c* is a detailed cross-sectional view taken from region C in FIG. 6*b;*
Figure 6D:
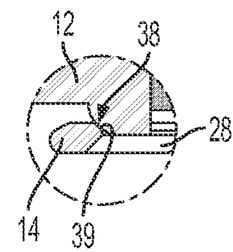
FIG. 6*d* is a detailed cross-sectional view taken from region D in FIG. 6*b;*

In order to make sure that the respective planar surfaces 32 and 34 of the MEMS unit 12 and the receptacle 14 remain in precise abutted contact, additional angular retention features 36 and 38 between the ball-in-socket connections 18 and 19 are additionally provided. As seen in FIGS. 6*b*-6*d*, the first angular retention feature 36 is formed on the MEMS unit 12 opposed from the biased connection 18 at the upper end thereof, and more particularly is defined at the closed end 27 of the slot 23 which forms the socket 24 receiving the biased ball 20 (see FIG. 4*a*). Acting opposed to this first angular retention feature 36 (i.e. facing in a opposite direction), is a second angular retention feature 38 which is jointly formed at the connection point between the receptacle 14 and the MEMS unit 12 at the lower end thereof, where the fixed catch element 26 is matingly received within the corresponding socket 28. This second angular retention feature 38 may be provided, for example, by the curved end wall 39 of the slot or socket 28 in the lower end of the receptacle 14. The angular retention features 36 and 38 therefore act in concert such as to keep the respective planar surfaces 32 and 34 of the MEMS unit 12 and the receptacle 14 in forced abutted contact, which in turn ensures that the orientations of the two components 12 and 14 are constrained about the X and Y axes. It is observed that the connection of the MEMS unit 12 to the receptacle 14 is predictable, using the connection features described above. Hence, it is possible to program the MEMS unit 12 of the preset type with an orientation related to the predicted orientation of the MEMS unit 12 in the receptacle 14. In doing so, the MEMS unit 12 could be pre-calibrated in such a way its orientation about at least one axis is known relative to a navigated feature of the instrument, when the preset MEMS unit 12 is activated or reset.

As described above, and referring again to FIGS. 7*a*-7*b*, the method of connected the MEMS navigation unit 12 and the receptacle 14 is performed by first aligning the rigid ball-in-socket connection feature 19 at the lower end of the two components 12 and 14 and matingly engaging this connection feature 19 by sliding the MEMS unit in direction A, and then pivoting or rotating the upper end of the MEMS unit 12 into the receptacle 14 in direction B such as to matingly engage the biased connection feature 18 at the upper end of the two components. The biased catch/ball 20 will be helped into reaching the socket 24 by moving along the ramp 27*a*. Once the biased catch/ball 20 of the upper connection feature 18 is snapped into engagement with its mating socket 24, the respective planar surfaces 32 and 34 of the MEMS unit 12 and the receptacle 14 are then in forced abutted contact, and the two components 12 and 14 are fastened together as shown in FIG. 7*b*. The MEMS navigation unit 12 and the receptacle 14 are thereby connected in precise engagement such that they are constrained in fixed position and orientation relative to each other.

While the interconnection system as described so far for fastening the MEMS navigation unit 12 within the receptacle 14 may be sufficient to maintain their alignment with precision and accuracy, in at least one embodiment of the present disclosure an additional, secondary, connection system is also provided to help maintain the MEMS navigation unit 12 within its receptacle 14 within established alignment precision and accuracy, which may be particularly useful during impaction and oscillatory vibration which sometimes occurs during surgery.

Figure 8:
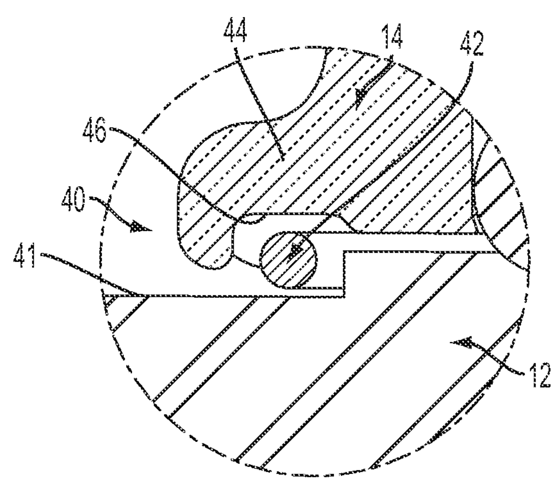
FIG. 8 is a cross-sectional view showing a first embodiment of a securing feature between the mated MEMS navigation unit and the receptacle.
Figures 9A, 9B:
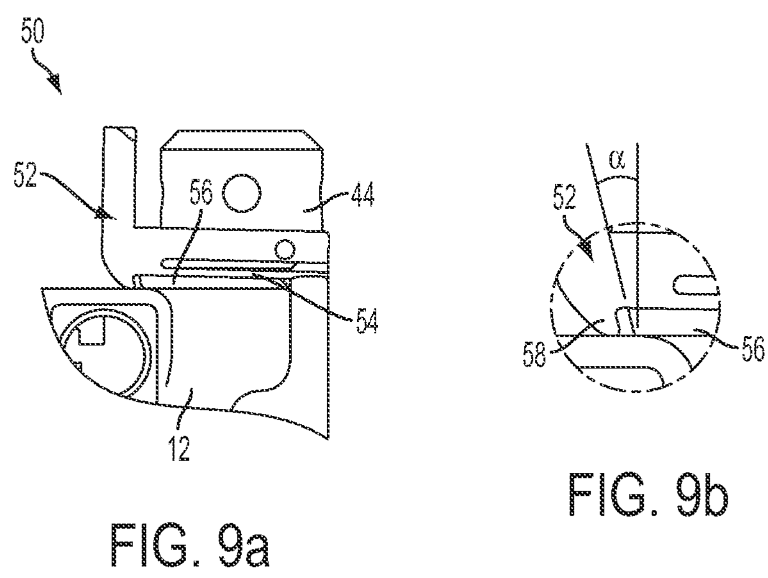
FIG. 9*a* is a cross-sectional view showing a second embodiment of the securing feature between the mated MEMS navigation unit and the receptacle.
FIG. 9*b* is a detailed cross-sectional view taken from region F in FIG. 9*a*.

Accordingly, referring particularly to FIGS. 8 to 9*b*, and also seen in FIG. 6*b*, a secondary connection system 40 is provided between the MEMS navigation unit 12 and the receptacle 14 which includes a compliant member 42 which is disposed between the upper surface 41 of the MEMS unit 12 and the facing upper rim 44 of the receptacle 14, such as to provide additional constraint in at least in a direction substantially parallel to the X-axis (see FIGS. 2*a*-2*b*). The compliant member 42 may include, for example, a wire-form or O-ring for example, and may either be substantially rigid or may be at least somewhat elastically deflectable. In either case, however, the compliant member 42 provides additional constraint in at least the X-axis direction to limit relative movement between the MEMS unit 12 and the receptacle 14, and may also provide damping therebetween such as to help absorb any vibrations.

In the event of impact or oscillatory vibration of the CAS tool to which the receptacle 14 is fixed, should the MEMS navigation unit 12 become slightly displaced within, or even momentarily disengaged from, the receptacle 14 (for example such that the biased catch/ball 20 become somewhat disengaged form its mating socket 24), MEMS navigation unit 12 will contact the compliant member 42 which will limit such displacement within the receptacle 14. The permitted displacement before the compliant member 42 comes into contact with the MEMS unit 12 may correspond to the limit at which the biased ball 20 can automatically return into its socket 24. During insertion of the MEMS unit 12 into the receptacle 14, the compliant member 42 will be moved upwards within its corresponding slot 46 in the upper rim 44 of the receptacle 14, as the MEMS navigation unit 12 is slid into its engaged position within the receptacle 14, whereupon the compliant member 42 will return to its original position as shown in FIG. 8.

In an alternate embodiment, an alternate secondary connection system 50 may be provided in lieu of, or possibly even in addition to, the connection system 40 described above. The alternate secondary connection system 50 also includes a compliant member in the form of a spring-return lever 52 which is mounted to the upper rim 44 of the receptacle 14 and includes a blade-spring 54 which is used to ensure that the lever 52 remains in continuous engaged contact with the top surface of the MEMS unit 12. The spring-return lever 52 operates in much the same manner as the compliant member 42 described above, in that it ensures that the MEMS unit 12 remains engaged in position and orientation within the receptacle 14 even if the other connection mechanisms (such as the biased catch/ball 20 of the connection device 18) become slightly disengaged. Accordingly, similar to the wire-form or other element of the compliant member 42, the spring-return lever 12 is moved upwards as the MEMS unit 12 is pushed into place within the receptacle, and then returns into a latched position (see FIG. 9*a*) wherein it is engaged with the top side edge of the MEMS navigation unit 12 once the MEMS unit 12 is completely connected in place within the receptacle 14. As seen in FIG. 9*b*, the lever 52 includes a latch feature 58 at its outer edge which engages the correspondingly shaped ridge 56 on the top side edge of the MEMS unit 12. The matching geometry of the ridge 56 on the MEMS unit 12 and the latch feature 58 on the lever 52 ensures that the MEMS unit 12 will not be disconnected from the receptacle during impaction and/or oscillatory vibration. To be able to disconnect the MEMS unit 12 from the receptacle 14, the lever 52 must be manually and voluntarily lifted by the user. This accordingly provides an additional secure and fail-safe interconnection between the MEMS navigation unit 12 and the receptacle 14.

The terms "top" and "bottom", "upward" and "downward", "vertical", etc., are generally used herein with reference to the orientation of the assembly 10 as shown in the drawings for ease of description purposes only, however it is to be understood that depending on the orientation of the instrument to which the receptacle 14 is fixed, these directions may not actually correspond to a true or absolute vertical, upward and/or downward direction.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. An inertial navigation assembly adapted for navigating a surgical instrument using a computer-assisted surgery CAS system remote from both the inertial navigation assembly and the surgical instrument, the CAS system being in wireless communication with the inertial navigation assembly, the navigation assembly comprising:

a micro-electromechanical sensor (MEMS) navigation unit having one or more MEMS producing at least orientation data and wirelessly transmitting the at least orientation data to the CAS system remote from the navigation assembly;

a support including a receptacle receiving the MEMS navigation unit therein, the support being adapted to be mounted on the instrument in a fixed orientation relative to established navigated features of the instrument; and at least two connection devices connecting and aligning the MEMS navigation unit and the support, a first connection device of the at least two connection devices including a pair of spaced apart mating ball-in-socket features disposed between the MEMS navigation unit and the support at opposed ends thereof for releasably engaging the MEMS navigation unit in precise orientational alignment within the receptacle, the pair of mating ball-in-socket features being aligned along an axis extending between the opposed ends, the pair of mating ball-in-socket features comprising a first ball-in-socket feature having a biased catch and a second ball-in socket feature having a fixed catch, the biased catch and the fixed catch being received within respective sockets formed within the MEMS navigation unit or the support.

2. The inertial navigation assembly according to claim 1, wherein the sockets of the ball-in-socket features being located in the receptacle of the support.

3. The inertial navigation assembly according to claim 2, wherein a second connection device of the at least two connection devices including at least one planar surface formed within the receptacle, the MEMS navigation unit being in coplanar abutment with the at least one planar surface when releasably engaged in the fixed orientation.

4. The inertial navigation assembly according to claim 3, wherein the receptacle comprises at least two planar surfaces for coplanar abutment with corresponding surfaces of the MEMS navigation unit, the two planar surfaces being transverse with respect to one another.

5. The inertial navigation assembly according to claim 4, wherein the receptacle comprises three planar surfaces arranged in a U, with normals of the planar abutment surfaces being transverse relative to said axis.

6. The inertial navigation assembly according to claim 1, wherein the fixed catch has a geometry defined by a sphere quarter merging with a half-cylinder.

7. The inertial navigation assembly according to claim 1, wherein the fixed catch protrudes from the MEMS navigation unit.

8. The inertial navigation assembly according to claim 1, wherein the biased catch is part of the support, and wherein the socket cooperating with the biased catch is on the MEMS navigation unit.

9. The inertial navigation assembly according to claim 8, wherein the socket is defined as a raised plateau on the MEMS navigation unit.

10. The inertial navigation assembly according to claim 9, wherein the MEMS navigation unit comprises a ramp portion adjacent to the socket and transitioning to the raised plateau for guiding the biased catch into the socket during assembly.

11. The inertial navigation assembly according to claim 9, further comprising an elastomer surrounding a periphery of the raised plateau in the releasable engagement.

12. The inertial navigation assembly according to claim 1, further comprising a latch feature on the support for latching engagement of the MEMS navigation unit to the support.

13. The inertial navigation assembly according to claim 12, wherein the latch feature comprises a lever for disengagement of the latch feature from the MEMS navigation unit.

14. The inertial navigation assembly according to claim 1, further comprising the instrument.

15. A method of using a micro-electromechanical sensor (MEMS) navigation unit of a computer-assisted surgery (CAS) system, the method comprising:

releasably engaging the MEMS navigation unit within a mating support fixed to a surgical instrument that is navigated by the CAS system, the support being in precise relative orientational alignment, and the CAS system being remote from both the MEMS navigation unit and the surgical instrument, comprising:

aligning and matingly engaging a pair of ball-in-socket features disposed between the MEMS navigation unit and the support at opposed ends thereof, the pair of ball-in-socket features being aligned relative to each other;

snap-fitting a biased catch of at least one of said ball-in-socket features within a corresponding socket to constrain and align the relative orientation of the MEMS navigation unit and the support together about a first axis; and wirelessly transmitting orientation data from the MEMS navigation unit to the CAS system without having calibrated the MEMS navigation unit position relative to the support.

16. The method according to claim 15, wherein releasably engaging the MEMS navigation unit further comprises abutting at least one planar surface on the MEMS navigation unit against a planar surface on a receptacle of the support, the planar surfaces lying in a substantially common plane to constrain the MEMS navigation unit and the support about at least a second axis.

17. The method according to claim 15, further comprising latching the MEMS navigation unit to the support when releasably engaging the MEMS navigation unit to the support.

* * * * *